United States Patent
Cheng

(10) Patent No.: US 7,485,137 B2
(45) Date of Patent: Feb. 3, 2009

(54) ELECTRIC HEAT THERAPY APPARATUS

(76) Inventor: Tzu-Chen Cheng, Av.27 de Hebrero, #418, Mirador Norte, La Feria, P.O. Box 165-2, Santo Domingo, D.N. (DO)

( * ) Notice: Subject to any disclaimer, the term of this patent is extended or adjusted under 35 U.S.C. 154(b) by 503 days.

(21) Appl. No.: 11/383,961

(22) Filed: May 18, 2006

(65) Prior Publication Data

US 2006/0212101 A1 Sep. 21, 2006

Related U.S. Application Data

(63) Continuation-in-part of application No. 10/347,099, filed on Jan. 17, 2003, now Pat. No. 7,097,655.

(51) Int. Cl.
*A61N 5/06* (2006.01)
(52) U.S. Cl. .............................. 607/90; 607/88; 607/96
(58) Field of Classification Search ................... 607/88, 607/90, 96; 606/9
See application file for complete search history.

(56) References Cited

U.S. PATENT DOCUMENTS

| | | | | |
|---|---|---|---|---|
| 2,490,074 A | * | 12/1949 | Marty | .......................... 601/18 |
| 3,089,033 A | * | 5/1963 | Fujisawa | ................. 250/504 R |
| 3,152,594 A | * | 10/1964 | Kramer | ........................ 607/90 |
| 3,792,230 A | * | 2/1974 | Ray | ............................ 392/410 |
| 4,159,411 A | * | 6/1979 | Ellersick | ..................... 392/410 |
| 4,505,545 A | * | 3/1985 | Salia-Munoz | ............... 359/896 |
| 4,658,283 A | * | 4/1987 | Koyama | ..................... 257/297 |
| 4,944,297 A | * | 7/1990 | Ratkoff et al. | ................ 607/96 |
| 5,643,333 A | * | 7/1997 | Yun | ............................ 607/88 |
| 5,691,543 A | * | 11/1997 | Ishizaka | ................ 250/559.06 |
| 2001/0047195 A1 | * | 11/2001 | Crossley | ...................... 607/88 |

* cited by examiner

*Primary Examiner*—Roy D Gibson
*Assistant Examiner*—Kaitlyn E Helling
(74) *Attorney, Agent, or Firm*—Leong C. Lei

(57) ABSTRACT

An electric heat therapy apparatus which includes an upper cover, a holder, a heating unit including a control circuit, an electrical connector and a light bulb, a heat reservoir, wherein the holder has no upper end connected to a lower ed of the upper cover and a lower end connected to an upper end of the electrical connector, the heat reservoir is connected to a lower end of the electrical connector, the heat reservoir has a closed bottom, and the light bulb is fitted within the heat reservoir for keeping heat and light in the heat reservoir, whereby the human skin can be prevented from causing pathological changes by the direct light given by the light bulb and the heat given by the light bulb will be efficiently retained in the heat reservoir and the temperature of the heat reservoir can be rapidly increased.

12 Claims, 6 Drawing Sheets

TEST RESULTS

| Heat Source | Time | Temperature | Temperature Increased | Heat Source | Time | Temperature | Temperature Increased |
|---|---|---|---|---|---|---|---|
| Light Bulb | 10分 | 66°C | 38°C | Heating Filament | 10分 | 42°C | 14°C |
| | 20分 | 90°C | 24°C | | 20分 | 64°C | 22°C |
| | 30分 | 102°C | 12°C | | 30分 | 80°C | 16°C |
| | 40分 | 109°C | 7°C | | 40分 | 88°C | 8°C |
| | 50分 | 113°C | 4°C | | 50分 | 91°C | 3°C |
| | 60分 | 115°C | 2°C | | 60分 | 93°C | 2°C |
| | 70分 | 116°C | 1°C | | 70分 | 94°C | 1°C |
| | 80分 | 116°C | 0°C | | 80分 | 94°C | 0°C |

1. Current : 0.12AMP
2. Voltage : 110V
3. Power : 13.2W
4. Environment : Room Temperature 28°C

FIG.6

ELECTRIC HEAT THERAPY APPARATUS

CROSS-REFERENCE

This is a continuation-in-part of the patent application Ser. No. 10/347,099, filed Jan. 17, 2003 U.S. Pat. No. 7,097,655 B2.

BACKGROUND OF THE INVENTION

1. Field of the Invention

This invention is related to an electric heat therapy apparatus which can prevent the human skin from direct light from the light source and can efficiently retain the heat in the heat reservoir.

2. Description of the Prior Art

Following the rapid change in society structures and booming in the business industry, people living in the current era has to fight with time. Being overstressed and lack of exercises become normal symptoms, thus people are usually suffering from muscle pains. To alleviate or combat muscle pain, different treatments have emerged, such as message, electrotherapy, heat treatment . . . etc. Taking heat treatment as an example, muscle pains are alleviated or cured by placing heat source device on human skin to allow the penetration of the heat into subcutaneous tissues; moreover, the heat treatment can even stimulate the human metabolism to further enhance the human health.

Generally, hot towels, hot packs, filled with chemical compositions, electric heat therapy devices, burners or the like are used for providing heat treatment. The electric heat therapy device is the most commonly used tool for heat treatment, because it can be conveniently used at home in irrespective of time and place and can be carried easily. The heat source for such an electric heat therapy device basically falls into two categories, i.e. the heating filament and the light bulb. As for the electric heat therapy device utilizing a light bulb as the heat source disclosed in U.S. Pat. Nos. 4,505,545 and 4,658,823 (see FIGS. 1 and 2), the electric heat therapy device 1 mainly includes a cylindrical body 11, 11a, a light bulb 12, 12a, and a power unit 13, 13a (only the electric heat therapy device 1 shown in FIG. 1 will be disclosed in the following).

The cylindrical body 11 has a closed end 111 and an open end 112. The power unit 13 is mounted on the inner side of the closed end 111 of the cylindrical body 11. The light bulb 12 is arranged against the open end 112 of the cylindrical body 11. When the power unit 13 supplies electricity to the light bulb 12, the light bulb 12 will give light to produce heat energy. Then, the open end 112 of the cylindrical body 11 is put onto the human body so that the human body will receive the light and heat given by the light bulb 12 simultaneously for heat treatment. Although the electric heat therapy device can achieve the heat treatment purpose, it still suffers from a lot of drawbacks. For instance, according to the latest medical report, direct light from the light bulb will cause pathological changes in the human skin. Hence, the electric heat therapy device connot bring good health to the user, but on the contrary, it will cause pathological changes in the human skin subject to direct light given by the light bulb. Furthermore, the electric heat therapy device suffers from a more serious drawback of losing most heat energy from the open end 112 of the cylindrical member 11 which has no means to reserve the heat energy, so that the electric heat therapy device will not be hot enough to provide workable heat treatment to the user.

Therefore, it is an object of the present invention to provide an improvement in the structure of am electric heat therapy apparatus which can obviate and mitigate the above-mentioned drawbacks.

SUMMARY OF THE INVENTION

This invention is related to an improvement in the structure of an electric heat therapy apparatus.

It is the primary object of the present invention to provide an electric heat therapy apparatus which includes an upper cover, a holder, a heating unit including a control circuit, an electrical connector and a light bulb, a heat reservoir, wherein the holder has an upper end connected to a lower end of the upper cover and a lower end connected to an upper end of the electrical connector, the heat reservoir is connected to a lower end of the electrical connector, the heat reservoir has a closed bottom, and the light bulb is fitted within the heat reservoir for keeping heat and light in the heat reservoir, whereby the human skin can be prevented from causing pathological changes by the direct light given by the light bulb and the heat given by the light bulb will be efficiently retained in the heat reservoir and the temperature of the heat reservoir can be rapidly increased.

It is another object of the present invention to provide an electric heat therapy apparatus wherein a plurality of radial through slots separated in horizontal and vertical directions are provided at the upper end of the heat reservoir and the electrical connector is made of a material which does not conduct heat thereby preventing heat from transferring to the holder from the heat reservoir and therefore achieving the purpose of convenient use.

It is a further object of the present invention to provide an electric heat therapy apparatus which can be used to give a massage to the human body thereby providing heat treatment and massage to the human body at the same time and therefore increasing circulation and promote relaxation to alleviate muscle pain and stimulating the human metabolism to further enhance the human health.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 6 illustrates test results according to the present invention.

DETAILED DESCRIPTION OF THE PREFERRED EMBODIMENT

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
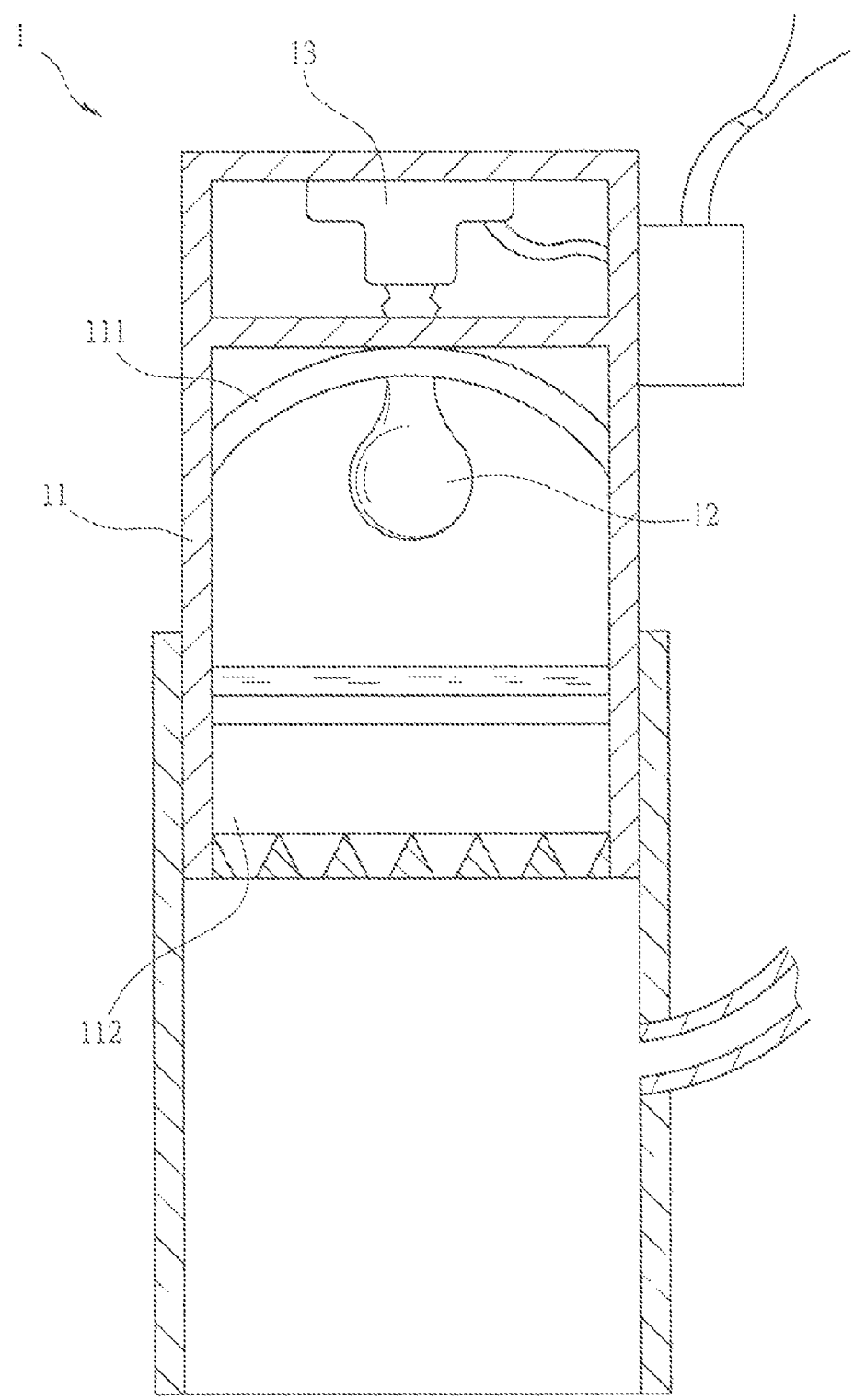
FIG. 1 illustrates an apparatus for applying light through an optical grid according to U.S. Pat. No. 4,505,545.
Figure 2:
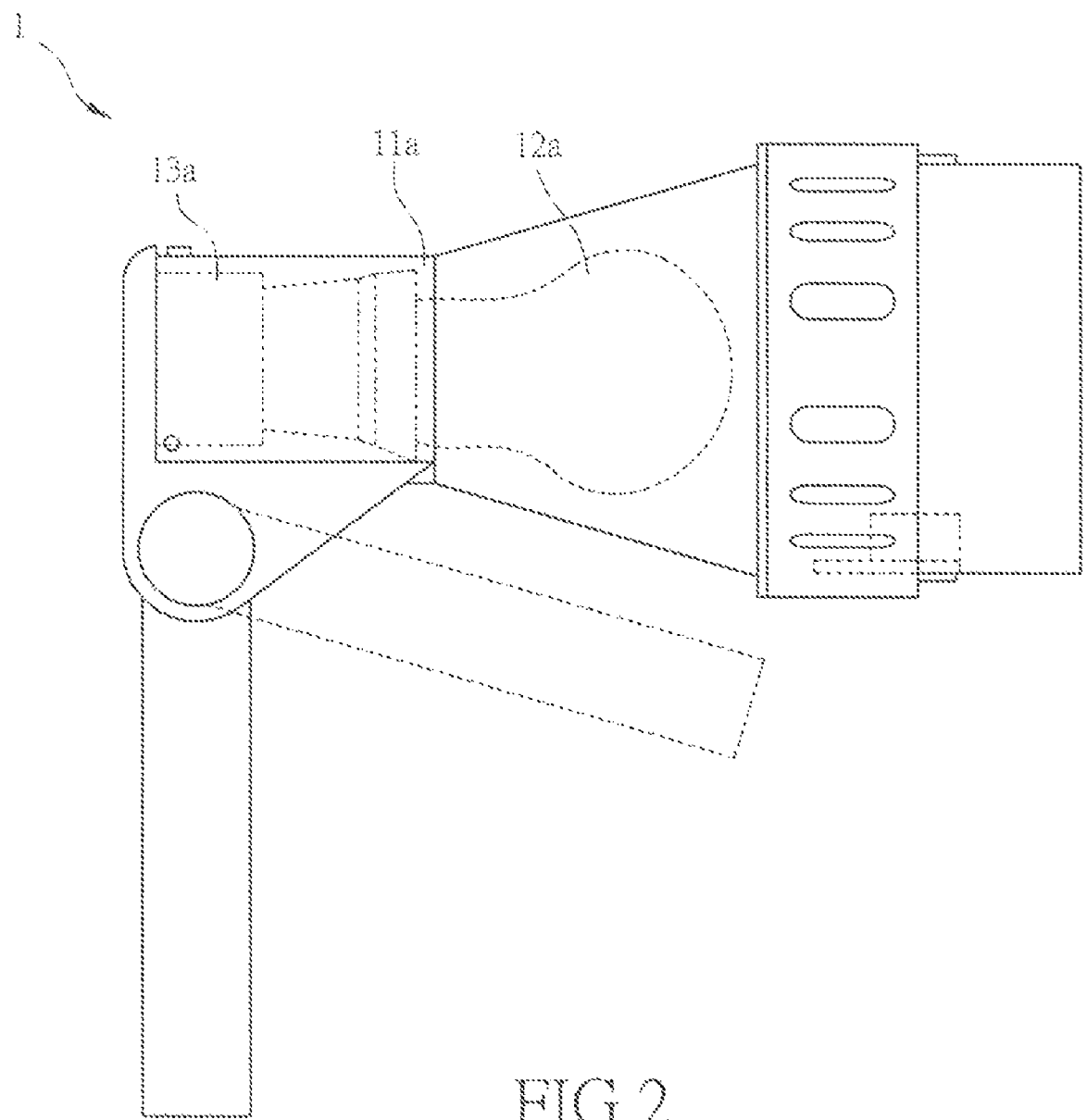
FIG. 2 illustrates an incandescent lamp structure for applying therapeutic heat according to U.S. Pat. No. 4,658,823.
Figure 3:
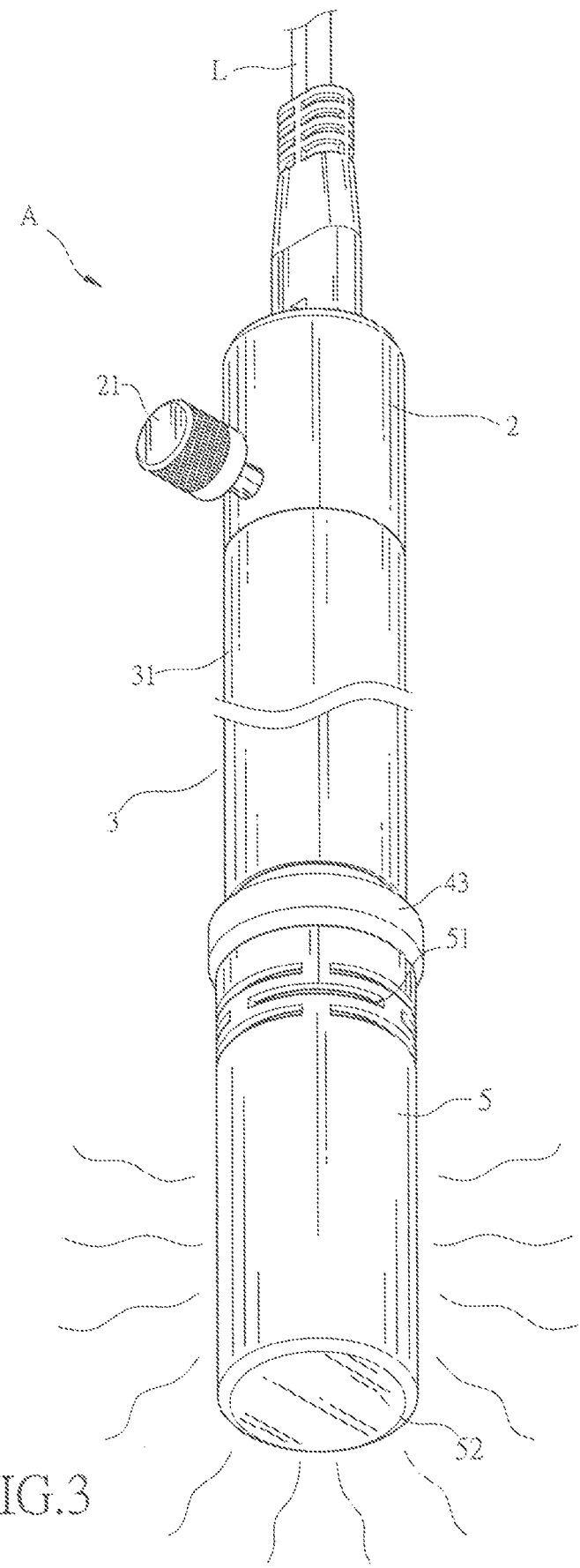
FIG. 3 is a perspective view of the present invention.
Figure 4:
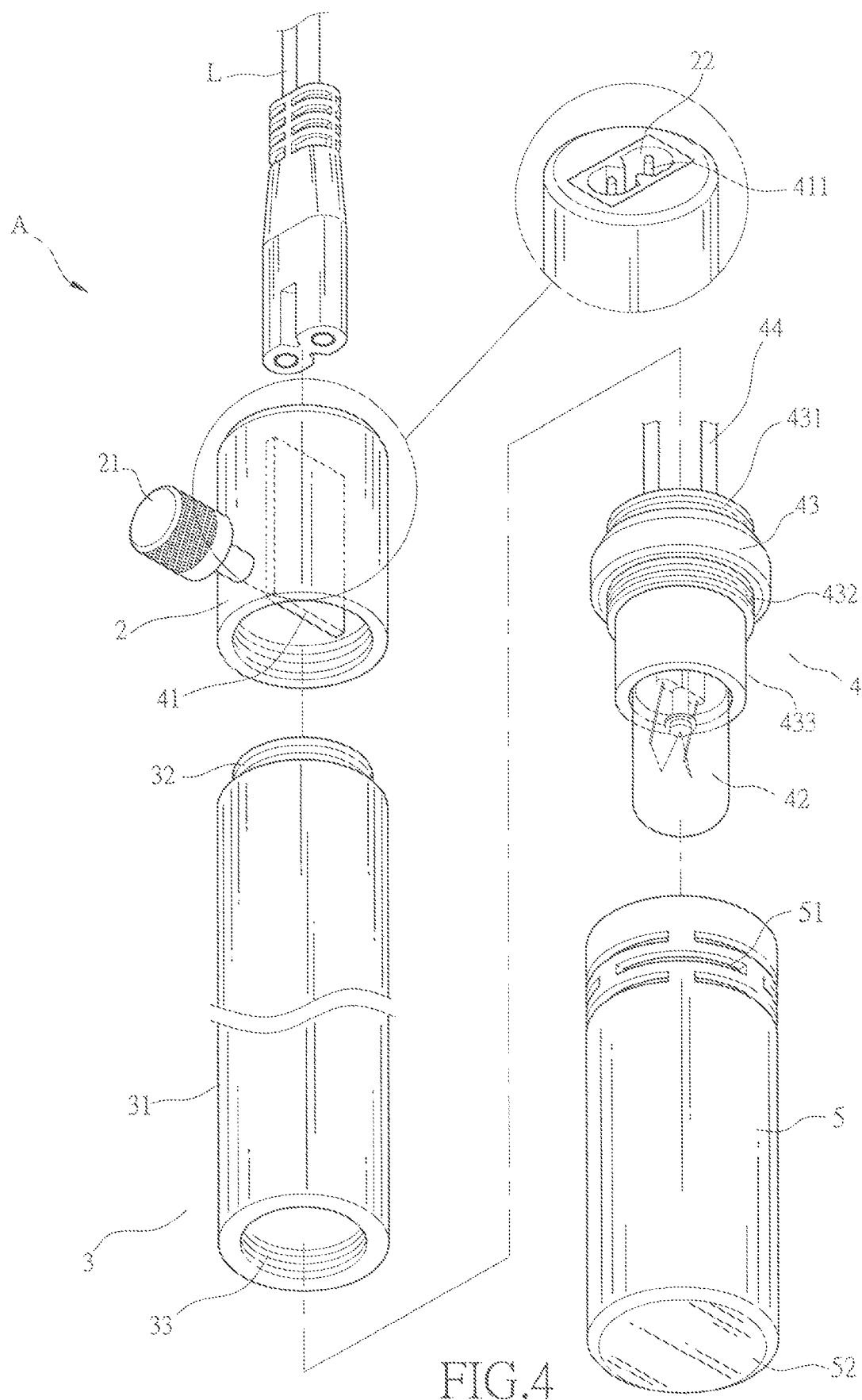
FIG. 4 is an exploded view of the present invention.
Figure 5:
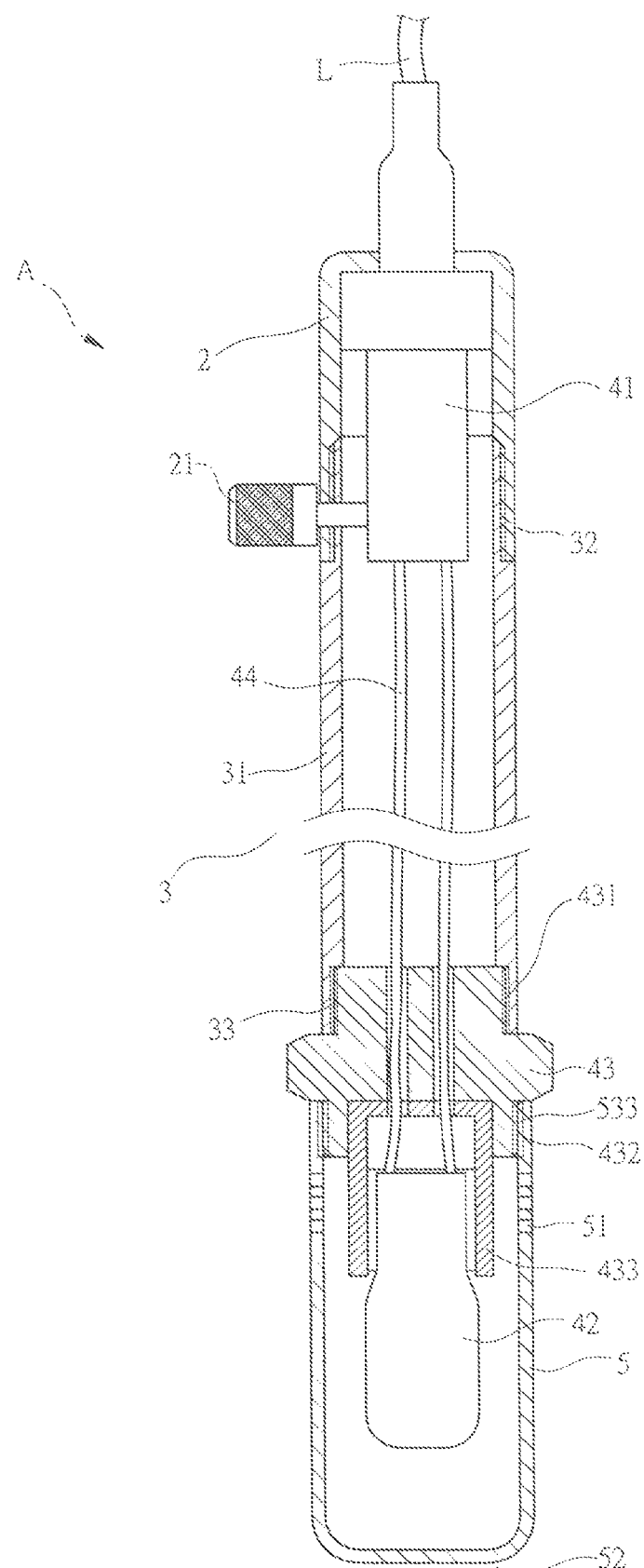
FIG. 5 is a sectional view of the present invention.

Referring to FIGS. 3, 4 and 5, the electric heat therapy apparatus A according to the present invention comprises an upper cover 2, a holder 3, a heating unit 4 and a heating reservoir 5.

The upper cover 2 is threadedly engaged with an upper end of the holder 3 and made of a material which does not conduct electricity and heat. The upper cover 2 is provided with a control switch 21 at one side. A control circuit 41 for controlling the light bulb 42 is arranged with the upper cover 2 and electrically connected with the control switch 21. By means of the control switch 21, the brightness of the light bulb 42 can be easily adjusted as desired thereby controlling the heat in the heating reservoir 5. The top end of the upper cover 2 is provided with a recess 22 in which are mounted two electrical terminals 411 for connecting with an electric cord L, sa as to supply electric power to the heat therapy apparatus A.

The holder 3 is a tubular member which may be made of metal and preferably of stainless steel. The holder 3 has a smooth outer surface 31 for holding and has an upper threaded end 32 and a lower threaded end 33. The upper threaded end 32 is threadedly engaged with the lower end of the upper cover 2, while the lower threaded end 33 is threadedly engaged with the upper threaded end 431 of the electrical connector 43.

The heating unit 4 comprises at least the control circuit 41, the light bulb 42 and the electrical connector 43. The control circuit 41 is mounted within the upper cover 2. The control circuit 41 is electrically connected with the electrical connector 43 via the electric cord 44 for supplying electric power to the electrical connector 43. The electrical connector 43 may be made of a material which does not conduct electricity and heat. The electrical connector 43 is provided with an upper threaded end 431 and a lower threaded end 432, wherein the former is connected with the lower end 33 of the holder 31, and the latter with the upper end of the heat reservoir 5. A cylindrical portion which is made of ceramic extends downwardly from the electrical connector 43 to form a seat 433 for receiving the light bulb 42 and is preferably made of ceramic.

The heat reservoir 5 is a tubular member having a closed bottom 52 and an open top and made of metal, preferably of stainless steel. The upper of the heat reservoir 5 is formed with a plurality of radial through slots 51 which are separated from each other in horizontal and vertical directions thereby preventing heat from conducting upwardly to the holder 3. The closed bottom 52 of the heat reservoir 5 is used for enclosing the light bulb 42 so as to prevent the light given by the light bulb 42 from going out of the heat reservoir 5 thus ensuring the heat given by the light bulb 42 to be efficiently retained in the heat reservoir 5 and therefore keeping the heat reservoir t at a high temperature and enabling the temperature to be rapidly raised. Furthermore, the heat reservoir 5 can prevent pathological changing of the human skin from direct light from the light bulb 42.

As shown in FIGS. 3 and 4, when in assembly, the upper cover 2 is first threadedly engaged with the upper end 32 of the holder 3 and then the lower end 33 of the holder 3 is threadedly engaged with the upper threaded end 431 of the electrical connector 43. Thereafter, the light bulb 42 is engaged with the seat 433 of the electrical connector 43 and the upper threaded end 533 of the heat reservoir 5 is engaged with the lower threaded end 432 of the electrical connector 43. Finally, the electric cord L is connected with the electrical terminals 411 in the recess 22 provided on the upper end of the upper cover 2. When the control switch 21 is turned on, the light bulb 42 will give heat energy which will be retained in the heat reservoir 5. As the temperature of the heat reservoir 5 reaches to a value capable for heat treatment, then the user may hold the body 31 of the holder 3 to put the heat reservoir 5 to a body portion where it is necessary to be heated. If the heat reservoir 5 is too hot, it is only necessary to wrap the heat reservoir with a piece of cloth, towel or the like before putting the heat reservoir 5 on the body so as to prevent from being scalded. Further, the user may move the heat reservoir 5 to and from on the body to give a massage to the body thereby providing heat treatment and massage to the body at the same time and therefore increasing circulation and promote relaxation to alleviate muscle pain and stimulating the human metabolism to further enhance the human health.

The present invention is first characterized by the heat reservoir 5 which encloses the light bulb 42 with its closed bottom thus preventing the human skin from pathological changes caused by direct light given by the light bulb 42. Moreover, as the light bulb 42 is enclosed within the heat reservoir 5, the light given by the light bulb 42 cannot go out of the heat reservoir 5 so that the heat given by the light bulb 42 will be efficiently retained in the heat reservoir 5 and the temperature of the heat reservoir 5 can be rapidly raised. FIG. 6 illustrates comparison test results from the light bulb 42 and the conventional heating filament. As can be seen, under the same conditions of power of 13.2 W (a current of 0.12 mp and a voltage of 110 v) and room temperature of 28° C., it is obvious that the temperature increased by the light bulb 42 enclosed within the heat reservoir 5 is higher than that by the conventional heating filament, though the heat energy must be converted into light which is than converted into heat energy.

Secondly, the present invention is characterized by the radial through slots 51 which are separated from each other in horizontal and vertical directions at the upper end of the heat reservoir 5 and by the electrical connector 43 which is made of a material that does not conduct heat so as to prevent the heat from transferring to the holder 3 from the heat reservoir 5.

Thirdly, the present invention is characterized in that the user may move the heat reservoir 5 to and from on the body to give a massage to the body thereby providing heat treatment and massage to the body at the same time and therefore increasing circulation and promote relaxation to alleviate muscle pain and stimulating the human metabolism to further enhance the human health.

It will be understood that each of the elements described above, or two or more together may also find useful application in other types of methods differing from the type described above.

While certain novel features of this invention has been shown and described and are pointed out in the annexed claim, it is not intended to be limited to the details above, since it will be understood that various omissions, modifications, substitutions and changes in the forms and details of the device illustrated and in its operation can be made by those skilled in the art without departing and in its operation can be made by those skilled in the art without departing in any way from the spirit of the present invention.

I claim:

1. An electric heat therapy apparatus comprising:
   an upper cover;
   a holder;
   a heating unit including a control circuit, an electrical connector and a light bulb engaged with said electrical connector;
   a heat reservoir;
   wherein said holder has an upper end connected to a lower end of said upper cover and a lower end connected to an upper end of said electrical connector, said heat reservoir has an open top and a closed bottom, said open top of said heat reservoir is connected to a lower end of said electrical connector, and said light bulb is fitted within said heat reservoir for keeping heat in said heat reservoir.

2. The electric heat therapy apparatus as claimed in claim 1, wherein
   said heat reservoir is provided with a plurality of radial through slots close to an upper end of said heat reservoir.

3. The electric heat therapy apparatus as claimed in claim 2, wherein
   said radial through slots which are separated from each other in horizontal and vertical directions.

4. The electric heat therapy apparatus as claimed in claim 1, wherein
   said upper cover is provided with a control switch electrically connected with said control circuit.

5. The electric heat therapy apparatus as claimed in claim 1, wherein
   said upper cover is provided with a recess in which are mounted electrical terminals.

6. The heat therapy apparatus as claimed in claim 1, wherein said
   electrical connector has a cylindrical portion made of ceramic and extending downwardly to form a seat for receiving said light bulb.

7. The electric heat therapy apparatus as claimed in claim 1, wherein
   said electrical connector is provided with an upper threaded end and a lower threaded end.

8. The electric heat therapy apparatus as claimed in claim 1, wherein
   said holder is provided with an upper threaded end and lower threaded end.

9. The electric heat therapy apparatus as claimed in claim 1, wherein
   said control circuit is mounted within said upper cover.

10. The electric heat therapy apparatus as claimed in claim 1, wherein
    said electrical connector is made of a material which does not conduct electricity and heat.

11. The electric heat therapy apparatus as claimed in claim 1, wherein
    said upper cover is made of a material which does not conduct electricity and heat.

12. The electric heat therapy apparatus as claimed in claim 1, wherein said holder and said heat reservoir is made of stainless steel.

* * * * *